(12) United States Patent
Stensrud et al.

(10) Patent No.: US 9,388,116 B2
(45) Date of Patent: Jul. 12, 2016

(54) ALCOHOL-MEDIATED ESTERIFICATION OF CARBOXYLIC ACIDS WITH CARBONATES

(71) Applicant: ARCHER DANIELS MIDLAND COMPANY, Decatur, IL (US)

(72) Inventors: Kenneth F. Stensrud, Decatur, IL (US); Mitchell J. Schultz, Decatur, IL (US); Padmesh Venkitasubramanian, Forsyth, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/437,750

(22) PCT Filed: Oct. 11, 2013

(86) PCT No.: PCT/US2013/064458
§ 371 (c)(1),
(2) Date: Apr. 22, 2015

(87) PCT Pub. No.: WO2014/070415
PCT Pub. Date: May 8, 2014

(65) Prior Publication Data
US 2015/0299095 A1    Oct. 22, 2015

Related U.S. Application Data

(60) Provisional application No. 61/719,537, filed on Oct. 29, 2012.

(51) Int. Cl.
*C07C 67/10* (2006.01)
*C07C 67/11* (2006.01)

(52) U.S. Cl.
CPC ............... *C07C 67/10* (2013.01); *C07C 67/11* (2013.01)

(58) Field of Classification Search
CPC ........ C07C 67/11; C07C 69/40; C07C 69/44; C07C 69/675; C07C 69/704; C07C 69/716; C07C 67/10; C07C 67/12; C07C 67/08
USPC ...................................... 560/1, 177, 180, 204
See application file for complete search history.

(56) References Cited

U.S. PATENT DOCUMENTS

| 5,783,723 | A | * | 7/1998 | Campbell | ............ C07C 67/343 |
| | | | | | 546/58 |
| 6,515,167 | B1 | * | 2/2003 | Shieh | ...................... C07C 67/10 |
| | | | | | 558/260 |
| 8,216,813 | B2 | * | 7/2012 | Thum | ...................... C12P 7/62 |
| | | | | | 435/132 |

(Continued)

OTHER PUBLICATIONS

Rivero "Esterification of Amino Acids and Mono Acids Using Triphosgene" Synthetic Communiations 31(14), 2169-2175 (2001).*

(Continued)

*Primary Examiner* — Jafar Parsa
*Assistant Examiner* — Amy C Bonaparte
(74) *Attorney, Agent, or Firm* — Vincent Kung

(57) ABSTRACT

A process for making esters from organic acids by means of reacting a carboxylic acid with dialkylcarbonate in an alcohol-containing solvent without any extrinsic acid or base catalyst is described. A benefit of the preparation process is that it can make the separation and extraction of ester products simpler and more facile vis-a-vis conventional isolation techniques.

19 Claims, 4 Drawing Sheets

(56) References Cited

U.S. PATENT DOCUMENTS

2010/0123097 A1* 5/2010 Belfadhel ............... C07C 67/11 252/182.12
2010/0144978 A1* 6/2010 Bevinakatti ............ C07C 67/11 525/418

OTHER PUBLICATIONS

Shieh "Nucleophilic Catalysis with 1,8-Diazabicyclo[5.4.0]undec-7-ene (DBU) for the Esterification of Carboxylic Acids with Dimethyl Carbonate" J. Org. Chem. 2002, 67, 2188-2191.*

Rekha "A Simple, Efficient, Green, Cost Effective and Chemoselective Process for the Esterification of Carboxylic Acids" Organic Process Research and Development 2009, 13, 769-773.*

Caretto "Upgrading Levulinic Acid with Dimethylcarbonate as Solvent/Reagent" ACS Sustainable Chem Eng 2013, 1, 989-994.*

Bartoli "Reaction of Dicarbonates with Carboxylic Acids Catalyzed by Weak Lewis Acids: General Method for the Synthesis of Anhydrides and Esters" Synthesis 2007 22, 3489-3496.*

Guerrero "1,2-Dimethylimidazole (DMI) and microwaves in the alkylation of carboxylic acids and p henosl with dimethyl and diethyl carbonates" ARKIVOC 2008, xi, 295-306.*

Awang "Enzymatic Synthesis of Palm Alkyl Ester Using Dialkyl Carbonate as an Alkyl Donors" American Journal of Applied Sciences 7(8), 2010, 1083-1086.*

Goossen "Lewis Acids as Highly Efficient Catalysts for the Decarboxylative Esterification of Carboxylic Acids with Dialkyl Carbonates" Adv. Synth. Catal. 2003, 345, 943-947.*

* cited by examiner

A. Succinic Acid

100% Conversion    60% Yield

B. Malic Acid

100% Conversion    79% Yield

C. Levulinic Acid

71% Conversion    70% Yield

D. Adipic Acid

100% Conversion    40% Yield    60% Yield

A. Succinic Acid

100% Conversion   54% Yield

B. Malic Acid

100% Conversion   69% Yield

C. Levulinic Acid

50% Conversion   47% Yield

D. Citric Acid

100% Conversion   46% Yield

E. Adipic Acid

100% Conversion   35% Yield   65% Yield

A.

83% conversion    1% yield

B.

100% conversion    10% yield

ALCOHOL-MEDIATED ESTERIFICATION OF CARBOXYLIC ACIDS WITH CARBONATES

CLAIM OF PRIORITY

The present Application is a national stage entry of International Application No. PCT/US2013/064458, filed 11 Oct. 2013, which claims benefit of U.S. Provisional Patent Application No. 61/719,537, filed on 29 Oct. 2012, the contents of each are herein incorporated by this reference.

FIELD OF INVENTION

The present invention relates to a chemical process for preparing esters from organic acids. In particular, the invention pertains to reactions of carboxylic acids with carbonates in a solvent to produce esters.

BACKGROUND

Esters are an important class of compounds that are encountered in various roles in all areas of synthetic organic chemistry. General methods of preparing esters start from carboxylic acids which are directly condensed with alcohol using acid catalysis (Fischer esterification). These prior esterification methods, in spite of their utility, suffer from several environmental drawbacks. Fischer esterification is an equilibrium process typically catalyzed by strong, corrosive, mineral acids (e.g., pKa<0). The water generated in the reaction has to be continuously removed by azeotroping or by use of a dehydrative agent or its role countered by use of a large excess of alcohol. Commonly used alcohols, such as methanol and ethanol, can generate genotoxic alkyl sulphates. Acylation and alkylation are inherently polluting because of salt generation, the use of toxic catalysts and reagents and use of chlorinated solvents.

In recent years chemists have looked to other ester preparation approaches that can be less polluting and more environmentally friendly. Dimethylcarbonate (DMC) has gained prominence as a "green" reagent in either acid- or base-catalyzed methylation or methoxycarbonylation of anilines, phenols, active methylene compounds and carboxylic acids. The attraction of DMC lies in the fact that it is non-toxic and gives rise only to $CO_2$ and methanol (recoverable) as the byproducts.

Several groups have proposed different approaches of using DMC in base-catalyzed methylation or methoxycarbonylation of anilines, phenols, active methylene compounds and carboxylic acids. Others have proposed a chemoselective process for the esterification of carboxylic acids under mild (~80°-90° C.) and solvent-free conditions using DMC and diethylcarbonate (DEC) under acid catalysis. (See, Vamsi V. Rekha et al., "A Simple, Efficient, Green, Cost Effective and Chemoselective Process for the Esterification of Carboxylic Acids," ORGANIC PROCESS RESEARCH & DEVELOPMENT, Vol. 13, No. 4, 769-773 (2009).) The process acquires the use of strong acids (i.e., pKa<0) such as $H_2SO_4$), or p-toluenesulfonic acid (PTSA), or mild acids such as m-toluic acid (MTA), which requires a downstream neutralization step prior to purification.

Another issue with current esterification reactions of organic acids with DMC is that they are often performed in dimethylformamide (DMF), which can be troublesome in post-synthesis downstream processing and purification, because of DMF's high boiling point (e.g., ~153° C.) and propensity to decompose overtime, which can lead to formation of highly toxic and reactive dimethylamine. This contamination of the desired ester products can be costly and harmful.

In view of the foregoing disadvantages a new process of esterification is needed, that can eliminate or minimize the issues associated with esterification reactions that depend on an extrinsic catalyst.

SUMMARY OF THE INVENTION

The present invention provides a method of preparing esters. The method involves the reaction of an organic acid with a diakylcarbonate in the presence of an alcohol-containing solvent and without either an extrinsic acidic or basic catalyst species. The method further comprises isolating the corresponding esters. The organic acid is a mono-, di-, tri-carboxylic acid or combination of such organic acids. The solvent is composed of an alcohol, a mixture of different alcohols, or a combination of an alcohol and a non-alcoholic species. The alcohol functions as a mediating agent in the reaction between the dialkylcarbonate and organic acid. Absent are an extrinsic acid or a base catalyst, as the inherent nucleophilicity of the alcohol drives the ester synthesis. Depending on the reaction species, one can produce monoesters, diesters, or triesters separately, or mixtures thereof in various combinations.

In another aspect the present invention relates to an ester compound formed from a reaction of a carboxylic acid with a carbonate in an alcohol-containing solvent without the presence of either an acid or base catalyst.

Additional features and advantages of the present methods will be disclosed in the following detailed description. It is understood that both the foregoing summary and the following detailed description and examples are merely representative of the invention, and are intended to provide an overview for understanding the invention as claimed.

DETAILED DESCRIPTION OF THE INVENTION

Section I—Description

In the present disclosure, we describe a facile, effective method of preparing esters from organic acids using environmentally friendly or so-called "green," non-toxic dialkylcarbonates (e.g., dimethyl or diethylcarbonates) in an alcoholic solvent (e.g., methanol or ethanol). The process of ester synthesis involves an alcohol-mediated reaction between an organic acid and a carbonate without the presence of either an extrinsic acid or base catalyst, conducted over relatively short reaction times. This approach is unprecedented in that no additional extrinsic acid or base catalysts are necessary to effect the esterification. Esterification of an organic acid with a dialkylcarbonate according to the present process results in high conversion rates (e.g., ≥50%) of the organic acid into its corresponding organic acid alkyl esters in relatively high yield (e.g., ≥35%). The alkyl esters can be easily isolated from the reaction mixture without need for neutralization, such as by means of at least fractional distillation, chromatography, or both. This process is achieved with a minimal amount of side products.

Figure 1:
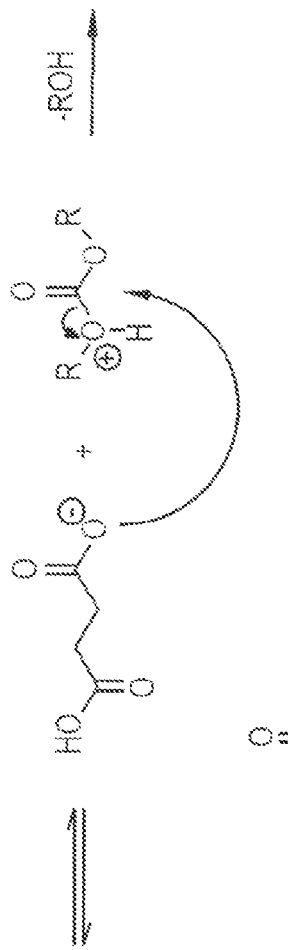
FIG. 1 is an illustration of an esterification reaction according to an iteration of the present process.

Although not bound by theory, FIG. 1 presents an illustration of a proposed, non-limiting mechanism for the present esterification reaction. In the proposed mechanism, the organic acid serves a dual role in the reaction. The organic acid itself serves, first, to activates the carbonate, and second, as a chemical reactant. Self-catalysis by the organic acid circumvents the need for an external catalyst. Additionally, the mechanism shows that an alcohol solvent/co-solvent serves as a reagent in the irreversible step of decomposition of the putative anhydride structure resulting in the formation of the product and $CO_2$.

In general, the present esterification reactions take advantage of solvolysis, in which the solvent serves as a reagent, driving the reaction forward by virtue of its great excess. For the esterification to proceed according to the present process, the solvent in the reaction is an alcohol. Solvolytic reactions entail nucleophilic substitutions (i.e., reactions in which an atom or a group of atoms in a molecule is replaced by another atom or group of atoms), where the electron rich solvents act as nucleophiles that add to then force the elimination of small molecules or group from the substrate.

Figure 2:
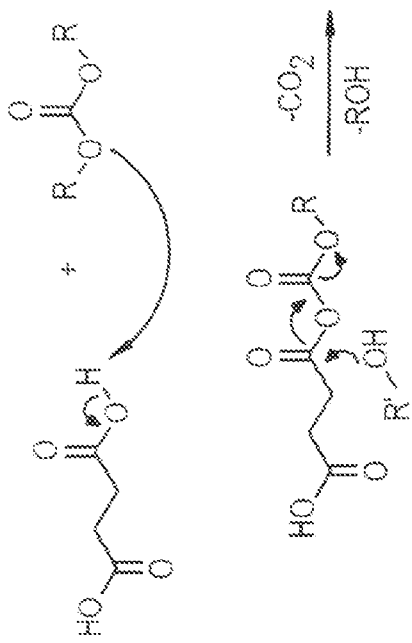
FIG. 2 is an illustration of a rate-limiting step for in-situ carbonate metathesis.

Unlike conventional esterification reactions, in the present method the alcohol-containing solvent does not function according to traditional nucleophile substitution mechanisms, in which the R-substituent of the alcohol directly displaces a leaving group. Not to be bound by theory, FIG. 2 illustrates a putative rate-limiting step of the present esterification reaction, which involves an in-situ generation of alkyl carbonates from dialkylcarbonates via a metathesis process, in which an anhydride ester is formed. This transient intermediate species in an intermolecular conversion rapidly decomposes in the presence of alcohol to a corresponding alkyl ester with the release of $CO_2$ and a molar equivalent of alcohol. The solvent-metathesized carbonate is the statistically favored product.

This result suggests that the alcohol species drives the ester formation through the decomposition of the anhydride intermediate, not the carbonate itself, as whatever carbonate one may start with will be altered depending on which kind of alcohol is used. In general, when carboxylic acids are reacted with a dialkylcarbonate in a corresponding alkyl alcohol, the alkyl-group of the alcohol appears to control which ester species is generated. For instance, when the alkyl-group of the dialkylcarbonate is different from that of the alcohol (e.g., DMC with ethanol) the resulting ester will predominately have alkyl groups similar to that of the alcohol (i.e., diethyl-ester). Hence, the presence of an alcohol-containing solvent is important for this process. The esterification reaction can be driven by an alcohol solvent alone or a mixed solvent containing an alcohol and a non-alcoholic species, and requires no extrinsic acid or base catalysts.

It appears that a greater amount of alcohol in excess of the amount of carbonate in a reaction will help drive the esterification to completion. Hence, in certain embodiments the amount of alcohol present is about 1.5- to 3-fold excess of the stoichiometric amount of carbonate. In other embodiments the amount of alcohol used is about 2- to 4-fold, or desirably about 5- to 7- or 10-fold excess of the stoichiometric amount of carbonate.

The stoichiometric amount of carbonate used in the reaction should be in excess equivalents of the number of carboxyl groups of the organic acid. At minimum the carbonate should be about 1.5 or 2 equivalents per carboxyl group. Typically, the amount of carbonate is about 2.5 equivalents or more, more typically about 3 to about 5 or 7 equivalents per carboxyl group.

The present esterification reaction of carboxylic acid with dialkycarbonate is performed typically in the liquid phase, in an alcohol-containing solvent. The particular amount of alcohol and species of alcohol may vary. The solvent may be composed entirely (i.e., 100%) of an alcohol or a mixture of different alcohols, or may comprise a mixture of an alcohol and a non-alcoholic species (e.g., an alcohol and $CO_2$ or carbonate mixture, which can generate in situ an active reagent). A certain amount of alcohol species in the solvent is required to perpetuate higher yields of the corresponding di-/mono-esters. The alcohol concentration in the solvent should be at least about 5% to about 10% by wt. of the solution.

A mixed solvent of alcohol and non-alcoholic species can produce a good yield of esters. The non-alcoholic component of the solvent can include an organic solvent, such as: carbonate/$CO_2$, dimethyl formamide (DMF), dimethyl sulfoxide (DMSO), acetonitrile, tetrahydrofuran (THF), acetone, N-methyl-2-pyrrolidone (NMP), chloroform, ethyl acetate, provided that the organic acids are at least partially soluble within them at the temperatures of the reaction.

For instance, when a mixed-solvent or blended system of DMF/alcohol, such as methanol is used in a 1:1 ratio, such as in Examples 7 and 20 of Table 3, the mixed solvent blend can help enhance substrate solubility for carbonate species that have a high molecular weight. In another example, a reaction mixture is prepared with $CO_2$ and methanol with a heterogeneous catalyst to generate a reaction product containing DMC and methanol. This reaction product can be part of a cost efficient and self-sustaining reagent system, and allows one to avoid the need to synthesis pure DMC. (For more detail about this process of converting $CO_2$ and methanol to DMC, see: Michael A. Pacheco, et al., "*Review of Dimethyl Carbonate (DMC) Manufacture and Its Characteristics as a Fuel Additive,*" ENERGY & FUELS 1997, 11, 2-19; Masayoshi Honda, et al., "*Catalytic Synthesis of Dialkyl Carbonate from Low Pressure $CO_2$ and Alcohols Combined with Acetonitrile Hydration Catalyzed by $CeO_2$,*" CATALYSIS A: GENERAL 384 (2010) 165-170; or Masayoshi Honda, et al., "*Ceria-Catalyzed Conversion of Carbon Dioxide into Dimethyl Carbonate with 2-Cyanopyridine.*" CHEMSUSCHEM, v. 6, issue 8, pp. 1341-1344 August 2013, the contents of each are incorporated herein by reference.)

Any liquid alcohol with R-groups having one to 12 carbons, or more, can serve as the solvent (reagent). The R-groups can be saturated, unsaturated, or aromatic. Alcohols such as methanol, ethanol, propanol, or butane are more typical in view of their common availability, inexpensiveness, and mechanistic simplicity in the esterification reaction. Table 1 shows non-limiting examples of some unsaturated and aromatic alcohols, which represent alternative species including their various permutations and derivatives. These alkene, alkyne, and aromatic alcohols are commercially available and relatively inexpensive.

TABLE 1

Unsaturated & Aromatic Alcohols

Alkene Alcohols

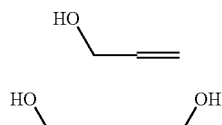

Alkyne Alcohols

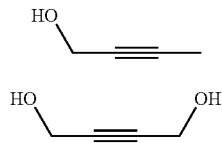

have an R-group with an identical number of carbon atoms as that of the dialkylcarbonate, such as ethanol reacting with diethylcarbonate.

Various alkylcarbonate species can be used in the esterification reaction according to the present process. The alkyl group in the dialkylcarbonate may have any number of carbon atoms, for instance, from 1 or 2 to 18 or 20 carbon atoms, typically between 1 and 15 carbon atoms, more typically between 1 and 10 carbon atoms. Preferably, the alkyl group has 1 to 6 carbon atoms. The alkyl group may, for example, be methyl, ethyl, n-propyl, isopropyl, n-butyl, iso-butyl, pentyl, isopentyl, hexyl, or isohexyl. Preferably, the alkyl is methyl or ethyl. Table 2 provides non-limiting examples of common dialkyl carbonate species, such as dimethylcarbonate (DMC), diethylcarbonate (DEC), dipropylcarbonate (DPC), or dibutylcarbonate (DBC), and their respective molecular weights and boiling points. For reasons of cost, common availability and ease of handling, dimethylcarbonate or diethylcarbonate are the carbonate species employed typically, but other dialkylcarbonate species may also be used.

TABLE 2

Carbonates

| Dialkylcarbonate | Boiling Pt. | Molecular Wt. | Structure |
|---|---|---|---|
| Dimethylcarbonate (DMC) | 90° C. | 90.08 g/mole | 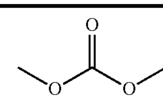 |
| Diethylcarbonate (DEC) | 126° C.-128° C. | 118.13 g/mole | 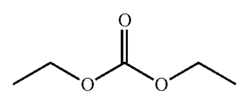 |
| Dipropylcarbonate (DPC) | 167° C.-168° C. | 146.18 g/mole | 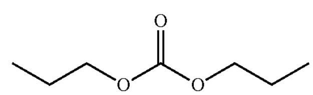 |
| Dibutylcarbonate (DBC) | 207.2° C. at 760 mmHg 95° C. at 15 mm Hg | 174.24 g/mole | 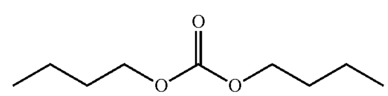 |

TABLE 1-continued

Unsaturated & Aromatic Alcohols

Aromatic Alcohols

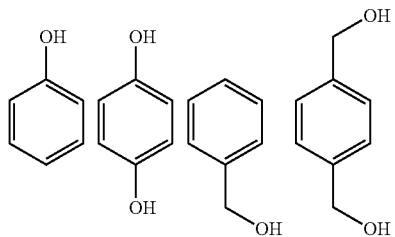

The particular choice of alcohol species can determine the kind of ester species generated. In certain embodiments, the alcohol may have an R-group different from that of the alkyl group in the dialkylcarbonate. For instance, when the alkyl group in the diakylcarbonate is a methyl group and the alcohol is an ethyl group. Alternatively, the alcohol species can One can use a variety of different organic acids, for example, selected from: a) monocarboxylic acids: formic acid, acetic acid, propionic acid, lactic acid, butyric acid, isobutyric acid, valeric acid, hexanoic acid, heptanoic acid, decanoic acid, lauric acid, myristic acid, and C14-C18 fatty acids; b) dicarboxylic acids: 2,5-furandicarboxylic acid (FDCA), fumaric acid, itaconic acid, malic acid, succinic acid, maleic acid, malonic acid, glutaric acid, glucaric acid, oxalic acid, adipic acid, pimelic acid, suberic acid, azelaic acid, sebacic acid, dodecanediocic acid, glutaconic acid, ortho-phthalic acid, isophthalic acid, terephthalic acid; or c) tricarboxylic acids: citric acid, isocitric acid, aconitric acid, tricarballylic acid, and trimesic acid. Desirably, the organic acid is a dicarboxylic or tricarboxylic acid. In certain preferred embodiments, the carboxylic acid can be selected from one or more of the following: succinic acid, malic acid, citric acid, levulinic acid, or adipic acid. As used herein an organic acid may be either a carboxylic acid or an amino acid.

The amount of reagents used in each reaction is adjusted to meet the requirements of the different organic acids. In other words, a mono-acid will need one equivalent of reagents, while a di-acid will use two equivalents, and a tri-acid will use three equivalents.

Typically, the reactions are performed within a time period not exceeding about 24 hours, often not exceeding about 10 or 12 hours, or preferably within about 6 or 8 hours, and more preferably within about 4 or 5 hours. For about each hour of increase in the duration of the reaction, the amount yield of ester product can improve about 5-10%.

The temperatures at which the esterification reaction is conducted may vary considerably, but usually the reaction temperature is in a range from about 130° C. to about 230° C., depending on the species of organic acid and dialkylcarbonate used in the reaction, in an inert atmosphere such as $N_2$. Typically, the temperature is in a range from about 140° C. or 150° C. to about 215° C. or 220° C. In certain embodiments the carboxylic acid and carbonate are reacted at a temperature between about 150° C. or 160° C. to about 208° C. or 215° C. Particular examples involve reactions at a temperature between about 165° C. or 168° C. to about 205° C. or 212° C. In other examples, the temperature is in a range from about 170° C. or 175° C. to about 200° C. or 210° C.; particularly, from about 180° C. or 185° C. to about 190° C. or 195° C.

Since the temperatures required to obtain good results in reasonable reaction times from an industrial point of view are generally higher than 120° C., and since the dialkylcarbonate (e.g., DMC, DEC, DPC, DBC) boils under such temperature ranges, the alkylation reactions are executed in an apparatus capable of bearing the required pressures.

The pressures at which the reaction is conducted are similarly susceptible to variation. Atmospheric and super-atmospheric pressures are generally applied, depending on the vapor pressure of the particular solvent at a particular temperature in the operative temperature range. Typically, the pressure is in a range from about 145 psi to about 950 psi; more typically from about 150 psi or 155 psi to about 900 psi or 920 psi (gauge), in certain examples the pressure is between about 160 psi and about 650 psi, or about 180 psi to about 620 psi. For instance, the vapor pressure of methanol is about 293.9 psi or 587.8 psi, respectively, at about 167.8° C. or 203.5° C. Ethanol, for example, has a vapor pressure of about 295 psi and 580 psi, respectively, at about 185° C. and 212° C.

According to the present process, one is able to achieve at least 50% conversion of a particular carboxylic acid to its corresponding mono-, di-, and tri-esters. Typically, the acid conversion rate is at least about 55%. More typically, the acid conversion rate is between about 60% and about 100%. Desirably, one is able to achieve at least 70% conversion. In some reactions, at least 50% of the organic acid is converted to a combined yield of monoesters and di-esters. Usually, the combined monoester and di-ester conversion rate is about 65% or greater. With optimization, complete conversions of carboxylic acids to their corresponding mono- and/or di-esters can be accomplished under the reaction conditions. The reaction can be performed in either a batch or continuous reaction process.

A principal advantage of the present method of esterification derives from the circumvention of added catalyst to effect complete acid or ester conversions. A corollary to this benefit is the simplification of downstream separation process for the reaction products in comparison to conventional techniques. One can eliminate a conventionally necessary downstream step of pH adjustment prior to purification. Moreover, the avoidance of either an extrinsic acidic or alkaline catalyst with the present synthesis process, one need not worry about the effects that acids or bases present in the distillation columns and one can recycle the distillation bottoms product back into the reaction.

The different organic acid esters produced in the esterification reaction can be isolated from the reaction mixture using various techniques such as by means of distillation or acid-base extraction. For instance, one can separate the mono and diesters, which tend to have boiling point of about 200° C. or greater, from lower boiling solvents by means of simple distillation, or use an acid-base extraction to precipitate the carboxylate, and then regenerate the organic acid with a strong acid (pKa<0, e.g., HCl).

Section II—Examples

According to the present esterification process, it is probable that in reactions involving diacids formation of monoesters would dominate during the initial stages of the reaction primarily due to statistics. Equation (1) represents an example of this mechanism involving a reaction of succinic acid with a diethylcarbonate in ethanol. According to the mechanism, if one di-acid molecule collides with two molecules of the carbonate, the di-ester would form. Statistically, however, it would be more likely that one molecule of the di-acid collides with one molecule of the carbonate, thus generating the monoester. Over time, the monoester would convert to corresponding di-esters.

Eq. (1)

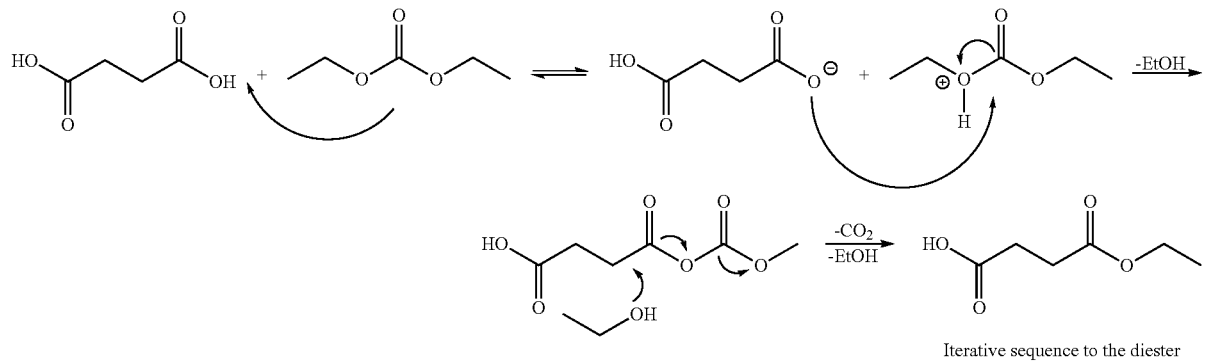

Iterative sequence to the diester

The ratio of monoesters to diesters produced can vary depending on the duration and temperature of the esterification reaction. Early in the reaction (i.e., 0-1 hours), the ratio significantly favors the monoester species (e.g., about 95:0.5). The ratio is about 4:1 after about 3-4 hours, and about 1:1-1:2.5 (depending on the acid and conditions) after 5 hours. This ratio would be about 1:3 or 1:4 after about 6-7 hours and about 0.5:95 after about 8-10 hours. Repeating these reactions will generate the di-ester or tri-ester of the corresponding di- or tri-acids.

Table 3 summarizes a number of comparative examples and inventive examples. In Comparative Examples 1 and 2, when an organic acid (e.g., succinic acid or levulinic acid) is reacted with an alcohol solvent alone, virtually no ester is produced, and the acid remains largely unreative. When the organic acid is reacted with a dialkyl carbonate in DMF solvent, as in Comparative Examples 3 and 4, the acid was again largely unreactive and generated a yield from about 0 wt. % to about 17 wt. % of ester.

bination of dialkyl carbonate species, the examples show that esters from each acid and carbonate combination can be prepared in relatively good yields (e.g., ≥45% or 50%) and with specificity (e.g., up to about ~79%±3% diester). The amount of ester produced and conversion of the acid are significantly greater than, e.g., 90%-100% conversion, up to about 80% yield vis-à-vis that of the comparative examples. Depending on particular reaction parameters, such as the temperature, pressure and duration of the esterification reaction, esters were produced with yields between about 43% or 45% and 75% or 80% by weight (e.g., 50% or 60% by wt.). With optimization of the process one can achieve even more favorable conversation rates and yields (e.g., about 90%, 95%, 97%, or 98% by weight).

TABLE 3

Experimental Results with Various Acid Species

| Example | Acid | Carbonate | Solvent | Ester | Ester Yield (%) | Acid Remaining (%) |
|---|---|---|---|---|---|---|
| Comp.1 | Succinic | None | methanol | Dimethylsuccinate | 0.0 | 90.8 |
| Comp.2 | Succinic | None | ethanol | Diethylsuccinate | 0.0 | 95.4 |
| Comp.3 | Succinic | DEC | DMF | Diethylsuccinate | 0.0 | 84.1 |
| Comp.4 | Succinic | DMC | DMF | Dimethylsuccinate | 16.3 | 52.3 |
| Comp.5 | Levulinic | DMC | DMC (neat) | Methyllevulinate | 10.0 | 0.0 |
| Comp.6 | Levulinic | DEC | DEC (neat) | Ethyllevaulinate | 1.1 | 17.2 |
| 1 | Succinic | DMC | Methanol | Dimethylsuccinate | 59.7 | 0.0 |
| 2 | Succinic | DMC | Ethanol | Diethylsuccinate | 56.5 | 8.7 |
| 3 | Succinic | DMC | Ethanol | Diethylsuccinate | 60.2 | 0.0 |
| 4 | Succinic | DEC | Methanol | Dimethylsuccinate | 53.9 | 0.0 |
| 4 | Succinic | DEC | Methanol | Dimethylsuccinate | 57.4 | 8.9 |
| 6 | Succinic | DEC | Methanol | Dimethylsuccinate | 61.5 | 0.0 |
| 7 | Succinic | DMC | Methanol/DMF | Dimethylsuccinate | 77.0 | 0.0 |
| 8 | Malic | DMC | Methanol | Dimethylmalate | 78.5 | 0.0 |
| 9 | Malic | DEC | Ethanol | Diethylmalate | 69.4 | 0.0 |
| 10 | Malic | DMC | Ethanol | Diethylmalate | 77.6 | 0.0 |
| 11 | Levulinic | DMC | Methanol | Methyllevulinate | 70.5 | 29.3 |
| 12 | Levulinic | DEC | Ethanol | Ethyllevulinate | 46.8 | 50.8 |
| 14 | Levulinic | DPC | Ethanol | Ethyllevulinate | 45.6 | 54.7 |
| 15 | Citric | DMC | Methanol | Trimethylcitrate | 71.3 | 0.0 |
| 16 | Citric | DEC | Ethanol | Triethylcitrate | 45.6 | 0.0 |
| 17 | Citric | DMC | Ethanol | Triethylcitrate | 55.8 | 0.0 |
| 18 | Adipic | DMC | Methanol | Dimethyladipate | 39.8 | 0.0 |
| 19 | Adipic | DEC | Ethanol | Diethyladipate | 35.1 | 0.0 |
| 20 | Adipic | DMC | Methanol/DMF | Dimethyladipate | 43.3 | 0.0 |

DMC = Dimethylcarbonate
DEC = Diethylcarbonate
DPC = Dipropylcarbonate
DMF = Dimethylformamaide
Reaction conditions: 20 g. acid. 5 molar equivalents of DMC/DEC/DPC (2.5 molar eq. in case of levulinic acid). 300 g. solvent reacted at 180° C., 5 h., 200 psi $N_2$.

When the esterification reaction is run without the presence of an alcohol we observe very little to no conversion of the carboxylic acid to its corresponding mono-ester, di-ester, tri-ester, or polyester. In the comparative examples, esterification reactions conducted neat in carbonate solvent resulted in negligible conversions of acid to ester product, such as in Comparative Examples 5 and 6 (i.e., levulinic acid ~10% wt. methyl esterification with DMC; ~1.1% wt ethyl esterification with DEC). Hence, alcohols appear to be an important reagent in the reaction so as to obtain a high-yielding esterification process (e.g., diester yield of ≥35%).

In contrast, the present esterification method can work well with a variety of different organic acids, in the examples conducted according to the present esterification reactions, we demonstrate that one can produce mono-, di- or tri-esters by means of reacting a corresponding carboxylic acid and dialkyl carbonate in an alcoholic solvent. Reacting five different carboxylic acids (i.e., mono-, di- and tri-acids: levulinic, succinic, malic, adipic, and citric acids) and a com- The following describe she preparation and reaction of some of the comparative and inventive examples in Table 3 in greater detail.

Example A

Synthesis of Diethyladipate from Adipic Acid, Diethylcarbonate, and Ethanol

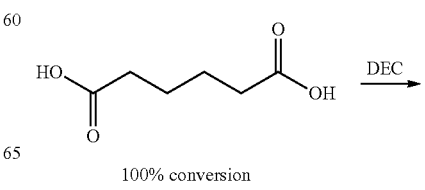

100% conversion

-continued

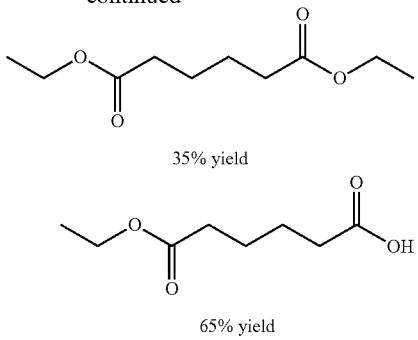

35% yield

65% yield

Twenty grams adipic acid, 83 mL of diethylcarbonate, and 300 g of ethanol were charged to a stainless steel, 1 L Parr reactor body. While stirring mechanically at 1100 rpm, the internal headspace was pressurized to 200 psi $N_2$ and heated to 180° C. for 5 h. After this time, the reactor body was cooled in a water bath until reaching room temperature and pressure released. The homogeneous solution was poured into a storage flask and a sample of this quantitatively analyzed for diethyladipate, mono-methyladipate and adipic acid.

Example B

Synthesis of Dimethylmalate from Malic Acid, Dimethylcarbonate, and Methanol

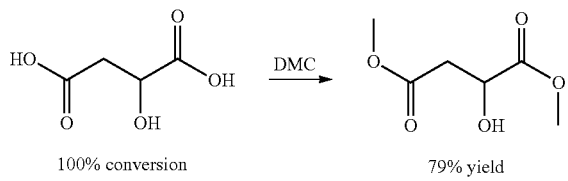

100% conversion          79% yield

Twenty grams malic acid, 63 mL of dimethylcarbonate, and 300 g of methanol were charged to a stainless steel, 1 L Parr reactor body. While stirring mechanically at 1100 rpm, the internal headspace was pressurized to 200 psi $N_2$ and heated to 180° C. for 5 h. After this time, the reactor body was cooled in a water bath until reaching room temperature and pressure released. The homogeneous solution was poured into a storage flask and a sample of this quantitatively analyzed for dimethylmatate and malic acid. Based on findings with adipic acid, the absence of malic acid in the product mixture and 79% yield of diester adduces the remaining 21% of product mixture as the corresponding mono-ester.

Example C

Synthesis of Methyllevulinate from Levulinic Acid and Dimethylcarbonate

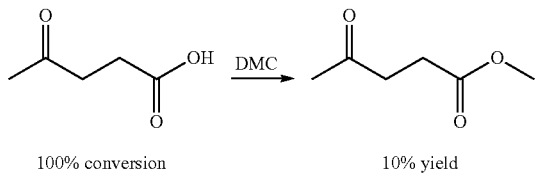

100% conversion          10% yield

Twenty grams levulinic acid and 300 g dimethylcarbonate were charged to a stainless steel, 1 L Parr reactor body. While stirring mechanically at 1100 rpm, the internal headspace was pressurized to 200 psi $N_2$ and heated to 180° C. for 5 h. After this time, the reactor body was cooled in a water bath until reaching room temperature and pressure released. The homogeneous solution was poured into a storage flask and a sample of this quantitatively analyzed for methyllevulinate and levulinic acid.

Example D

Synthesis of Dimethylsuccinate from Succinic Acid, Dimethylcarbonate, and Dimethylformamide

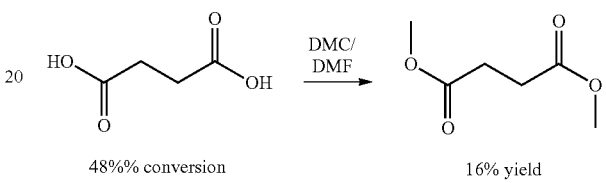

48%% conversion          16% yield

Twenty grams succinic acid, 72 mL dimethylcarbonate and 300 g of DMF were charged to a stainless steel, 1 Parr reactor body. While stirring mechanically at 1100 rpm, the internal headspace was pressurized to 200 psi $N_2$ and heated to 180° C. for 5 h. After this time, the reactor body was cooled in a water bath until reaching room temperature and pressure released. The homogeneous solution was poured into a storage flask and a sample of this quantitatively analyzed for dimethylsuccinate and succinic acid.

The accompanying Tables 4-7 summarize examples of the synthesis of di-esters from dimethyl carbonate and diethyl carbonate using succinic acid and either methanol or ethanol solvent. In Table 4, succinic acid is reacted with dimethylcarbonate in ethanol at a temperature of about 180° C. in an inert nitrogen atmosphere at a pressure of 500 psig. The di-ester product is predominately diethylsuccinate at about 56.5% yield with minimal dimethylsuccinate at 0.1% yield. A small amount of succinic acid remained unreacted. In contrast, in Table 5, succinic acid is reacted with diethylcarbonate and methanol at 190° C. under similar conditions. The di-ester product is overwhelmingly dimethylsuccinate at about 57.64% yield, with minimal diethylsuccinate at 0.0% yield. Table 6 presents a reaction of succinic acid with diethylcarbonate in ethanol at 190° C. for 5 hours, which produced diethylsuccinate at about 52.5% conversion. Table 7 summarizes the results of a reaction between citric acid and diethylcarbonate in ethanol at a temperature of 190° C. for about 5 hours in an inert atmosphere at a pressure of about 500 psig. The reaction produced triethylcitrate at about 38% conversion. All of the citric acid was consumed. As the examples show in these tables, esterification conducted under mild conditions according to the present process produces various kinds di-esters and tri-esters from different organic acids at relatively good conversion rates. The ester yields will improve with adjustments to increase the reaction time and/or temperatures for optimal results.

Figure 3:
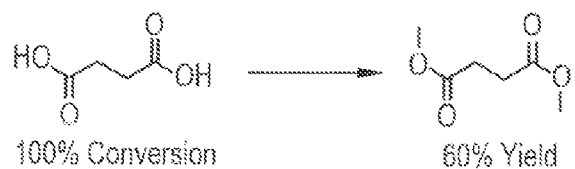
FIG. 3 shows a set of esterification reactions in which various carboxylic acids are reacted with methylcarbonate in methanol, according to an embodiment of the present invention.
Figure 3:
Figure 3:
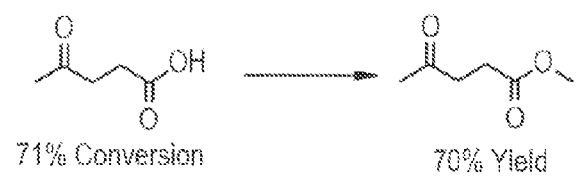
Figure 3:
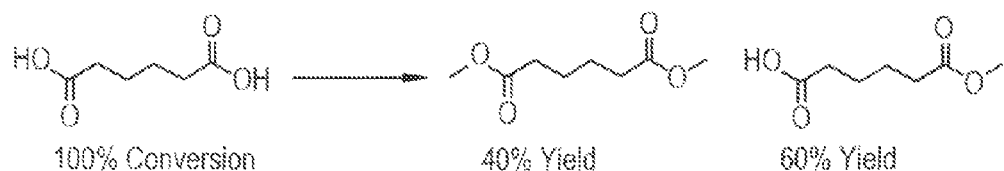

FIG. 3 presents a series of methyl esterification reactions using various kinds of carboxylic acids with dimethylcarbonate in methanol. Each reaction used 20 g. carboxylic acid, 5 molar equivalents of dimethylcarbonate (DMC) (2.5 equivalents for levulinic acid), 300 g. of absolute methanol, at 180° C. 5 h, 200 psi $N_2$. All acids, except levulinic acid, completely converted in the reaction. Each exhibited high selectivity (e.g., 40%) of the fully esterified target (diester) species. FIGS. 3A and 3B represent esterification of succinic acid and malic acid, respectively, which produced about a yield of about 60% and 79%, respectively, of the corresponding di-esters. In FIG. 3C, about 71% of levulinic acid was consumed in the reaction to produce about 70% yield of the ester. The esterification reaction with adipic acid produced a mixed product of the corresponding mono-ester and di-ester, respectively, at about 60% and 40% yield.

Figure 4:
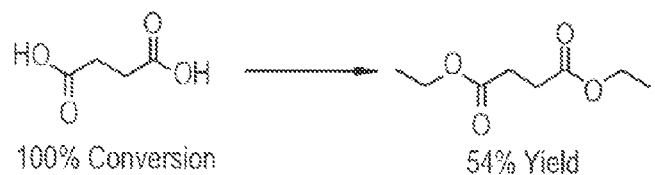
FIG. 4 shows a set of esterification reactions in which various carboxylic acids are reacted with diethylcarbonate in ethanol, according to an embodiment of the present invention.
Figure 4:
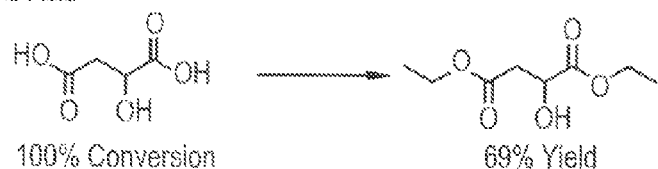
Figure 4:
Figure 4:
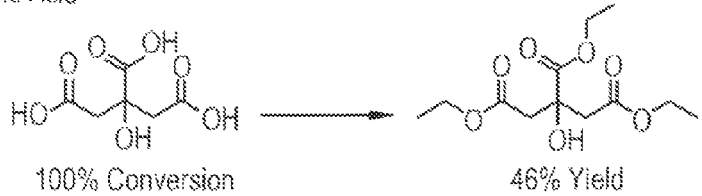
Figure 4:
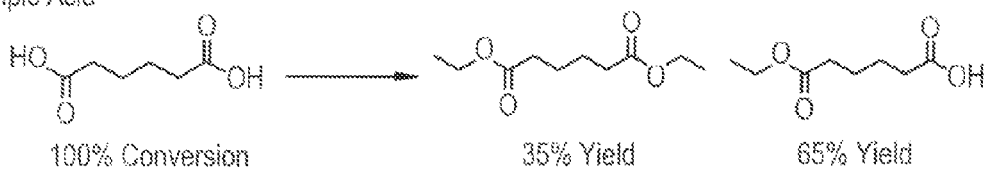

Similar to the reactions in FIG. 3, FIG. 4 presents a number of reactions in which different ethyl esters of carboxylic acids are prepared with diethylcarbonate in ethanol. The each of the reactions was performed with 20 g. carboxylic acid, 5 molar equivalents of diethylcarbonate (DEC) (2.5 equivalents for levulinic acid, 300 g. ethanol, at 180° C., 5 h, 200 psi $N_2$. Again all acids, except levulinic acid, manifested complete conversion during the respective reactions. The selectivity for each of the esterified targets was very good, at about 35% or greater. FIG. 4A shows the esterification of succinic acid, which produced a yield of about 54% of the corresponding di-ester. In FIG. 4B, malic acid is also completely consumed and produced a yield of about 69% of the corresponding di-ester. In FIG. 4C, about 50% of the levulinic acid is consumed to yield about 47% of the corresponding ester. In FIG. 4D, citric acid completely converted to produce about 46% of the tri-ester. FIG. 4E shows the reaction of adipic acid to make a mixed product of the corresponding monoester and di-ester, about 65% and 35%, respectively. The remaining product in each ease, excepting levulinic aid, presumably is the mono-ester.

Figure 5:
FIG. 5 shows a comparative set of esterification reactions in which levulinic acid is reacted in neat carbonates without an alcoholic solvent.
Figure 5:
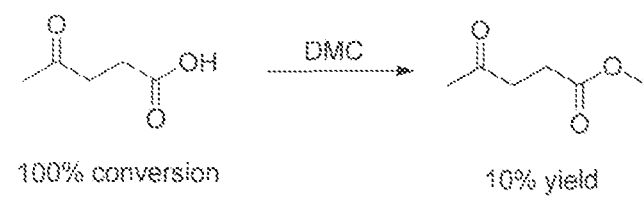

FIGS. 5A and 5B illustrate comparative examples (entries 5 and 6 of Table 3) in which levulinic acid is reacted, respectively, with diethylcarbonate and dimethylcarbonate without any other solvent being added. The reactions were performed with 50 g. carboxylic acid, 300 g. of diethylcarbonate (DEC/dimethylcarbonate (DMC) (respectively 5.9, 7.7 molar equivalents), at 180° C., 5 h, 200 psi $N_2$. The reactions in the comparative examples both exhibited relatively high conversion (~80%) of the organic acid, but low yield of ester, which indicates an ineffective method of esterification. The reactions generated a very small amount of ester (~1%) when using DEC, and made a slightly better but still minor amount of ester (≤10%) when using DMC. The difference in yield obtained between the reactions that employed DMC versus DEC is likely a result of steric hindrance to the bimolecular substitution in the reaction.

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

TABLE 4

Esterification of Succinic Acid with Dimethylcarbonate in Ethanol

| | | | | |
|---|---|---|---|---|
| Example: | 1 | | | |
| Mass of Succinic Acid (g): | 20 | | | |
| Molecular weight succinic acid (g/mol) | 118.04 | | | |
| Moles of Succinic Acid | 0.17 | | | |
| Molar equivalents of Dimethylcarbonate | 5 | | | |
| Mass of Dimethylcarbonate (g) | 76.31 | | | |
| Molecular weight Dimethylcarbonate (g/mol) | 90.08 | | | |
| Moles of Diethylcarbonate | 0.85 | | | |
| Density of Dimethylcarbonate (g/mL) | 1.07 | | | |
| Volume of Dimethylcarbonate (mL) | 71.32 | | | |
| Mass of Ethanol (g) | 300 | | | |
| Density of Ethanol (g/mL) | 0.789 | | | |
| Volume of Ethanol (mL) | 380.23 | | | |
| Total Volume (mL) | ~451.55 | | | |
| Total Mass (g) | 396.31 | | | |
| Reaction Temperature (° C.) | 180 | | | |
| Reaction Time (h) | 5 | | | |
| Initial $N_2$ Pressure (psig) | 200 | | | |
| $N_2$ Pressure at 180° C. (psig) | 500 | | | |
| Molecular weight dimethyl succinate (g/mol) | 146.14 | | | |
| Molecular weight diethyl succinate (g/mol) | 174.19 | | | |
| Results are in g/L | Dimethylsuccinate (g/L) | Mass dimethyl succinate (g) | Moles dimethyl succinate | % Conversion |
| | 0.041 | 0.0185 | 0.0001 | 0.1% |
| Results are in g/L | Diethylsuccinate (g/L) | Mass diethylsuccinate (g) | Moles diethyl succinate | % Yield |
| | 36.9 | 16.6622 | 0.0957 | 56.5% |
| Results are in g/kg | Succinic Acid Remaining (g/kg) | Mass Succinic Acid (g) | Moles Succinic Acid | % Succinic Acid Remaining |
| | 4.41 | 1.7477 | 0.0148 | 8.7% |

TABLE 5

Esterification of Succinic Acid with Diethylcarbonate in Methanol

| | |
|---|---|
| Example: | 1 |
| Mass of Succinic Acid (g): | 20 |
| Molecular weight succinic acid (g/mol) | 118.04 |
| Moles of Succinic Acid | 0.169 |
| Molar equivalents of Diethylcarbonate | 5 |

TABLE 5-continued

Esterification of Succinic Acid with Diethylcarbonate in Methanol

| | | | | |
|---|---|---|---|---|
| Mass of Diethylcarbonate (g) | 100.31 | | | |
| Molecular weight diethylcarbonate (g/mol) | 118.13 | | | |
| Moles of Diethylcarbonate | 0.847 | | | |
| Density of Diethylcarbonate (g/mL) | 0.975 | | | |
| Volume of Diethylcarbonate (mL) | 103 | | | |
| Mass of Methanol (g) | 300 | | | |
| Density of Methanol (g/mL) | 0.792 | | | |
| Volume of Methanol (mL) | 378.79 | | | |
| Total Volume (mL) | ~481.79 | | | |
| Total Mass (g) | 420.31 | | | |
| Reaction Temperature (° C.) | 190 | | | |
| Reaction Time (h) | 5 | | | |
| Initial $N_2$ Pressure (psig) | 200 | | | |
| $N_2$ Pressure at 180° C. (psig) | 500 | | | |
| Molecular weight diethyl succinate (g/mol) | 174.19 | | | |
| Molecular weight dimethyl succinate (g/mol) | 146.14 | | | |
| Results are in g/L | Diethylsuccinate (g/L) | Mass diethyl succinate (g) | Moles diethyl succinate | % Conversion |
| | 0.00 | 0.0014 | 0.0000 | 0.0% |
| Results are in g/L | Dimethylsuccinate (g/L) | Mass dimethylsuccinate (g) | Moles dimethyl succinate | % Yield |
| | 29.40 | 14.1646 | 0.0969 | 57.64% |
| Results are in g/kg | Succinic Acid Remaining (g/kg) | Mass Succinic Acid (g) | Moles Succinic Acid | % Succinic Acid Remaining |
| | 4.22 | 1.7737 | 0.0150 | 8.9% |

TABLE 6

Esterification of Succinic Acid with Diethylcarbonate in Ethanol

| | | | | |
|---|---|---|---|---|
| Example: | 1 | | | |
| Mass of Succinic Acid (g): | 20 | | | |
| Molecular weight succinic acid (g/mol) | 118.04 | | | |
| Moles of Succinic Acid | 0.169 | | | |
| Molar equivalents of Diethylcarbonate | 5 | | | |
| Mass of Diethylcarbonate (g) | 100.31 | | | |
| Moles of Diethylcarbonate | 0.847 | | | |
| Density of Diethylcarbonate (g/mL) | 0.975 | | | |
| Volume of Diethylcarbonate (mL) | 103 | | | |
| Mass of Ethanol (g) | 300 | | | |
| Density of Ethanol (g/mL) | 0.789 | | | |
| Volume of Ethanol (mL) | 380 | | | |
| Total Volume (mL) | ~490 | | | |
| Total Mass (g) | 420.31 | | | |
| Reaction Temperature (° C.) | 190 | | | |
| Reaction Time (h) | 5 | | | |
| Initial $N_2$ Pressure (psig) | 200 | | | |
| $N_2$ Pressure at 190° C. (psig) | 500 | | | |
| Molecular weight diethyl succinate (g/mol) | 174.19 | | | |
| Results are in g/L | Diethylsuccinate (g/L) | Mass diethyl succinate (g) | Moles diethyl succinate | % Conversion |
| | 32.00 | 15.46 | 0.0888 | 52.2% |
| Results are in g/kg | Succinic Acid Remaining (g/kg) | Mass Succinic Acid (g) | Moles Succinic Acid | % Succinic Acid Remaining |
| | 2.3 | 0.966713 | 0.0082 | 4.8% |

TABLE 7

Esterification of Citric Acid with Diethylcarbonate in Ethanol

| | |
|---|---|
| Example: | 1 |
| Mass of Citric Acid (g): | 20 |
| Molecular weight succinic acid (g/mol) | 192.12 |
| Moles of Citric Acid | 0.104 |
| Molar equivalents of Diethylcarbonate | 6 |
| Mass of Diethylcarbonate (g) | 73.78 |
| Moles of Diethylcarbonate | 0.625 |
| Density of Diethylcarbonate (g/mL) | 0.975 |
| Volume of Diethylcarbonate (mL) | 75.68 |
| Mass of Ethanol (g) | 300 |
| Density of Ethanol (g/mL) | 0.789 |
| Volume of Ethanol (mL) | 380 |

TABLE 7-continued

Esterification of Citric Acid with Diethylcarbonate in Ethanol

| | | | | |
|---|---|---|---|---|
| Total Volume (mL) | ~455 | | | |
| Total Mass (g) | 393.78 | | | |
| Total Mass (kg) | 0.39378 | | | |
| Reaction Temperature (° C.) | 190 | | | |
| Reaction Time (h) | 5 | | | |
| Initial $N_2$ Pressure (psig) | 200 | | | |
| $N_2$ Pressure at 190° C. (psig) | 500 | | | |
| Molecular weight diethyl succinate (g/mol) | 118.13 | | | |
| Results are in g/L | Triethylcitrate (g/L) | Mass triethylcitrate (g) | Moles triethylcitrate | % Conversion |
| | 32.00 | 15.46 | 0.0888 | 38.0% |
| Results are in g/kg | Citric Acid Remaining (g/kg) | Mass Citric Acid (g) | Moles Citric Acid | % Citric Acid Remaining |
| | 0 | 0 | 0.0000 | 0.0% |

We claim:

1. A method of preparing esters comprising: contacting an organic acid and a dialkylcarbonate in a reaction mixture with an alcohol-containing solvent absent an extrinsic catalyst at a temperature and for a time sufficient to produce esters, wherein said dialkylcarbonate is at least one of the following species: dimethylcarbonate (DMC), diethylcarbonate (DEC), dipropylcarbonate (DPC), or dibutylcarbonate (DBC).

2. The method according to claim 1, wherein said organic acid is a dicarboxylic or tricarboxylic acid.

3. The method according to claim 1, wherein said organic acid is selected from the group consisting of: formic acid, acetic acid, propionic acid, lactic acid, butyric acid, isobutyric acid, valeric acid, hexanoic acid, heptanoic acid, decanoic acid, lauric acid, myristic acid, $C_{14}$-$C_{18}$ fatty acids, 2,5-furandicarboxylic acid (FDCA), fumaric acid, itaconic acid, malic acid, succinic acid, maleic acid, malonic acid, glutaric acid, glucaric acid, oxalic acid, adipic acid, pimelic acid, suberic acid, azelaic acid, sebacic acid, dodecanedioic acid, glutaconic acid, ortho-phthalic acid, isophthalic acid, terephthalic acid, citric acid, isocitric acid, aconitic acid, tricarballylic acid, and trimesic acid.

4. The method according to claim 1, wherein said alcohol-containing solvent includes a single alcohol species, a mixture of different alcohols, or a mixture of an alcohol and other non-alcoholic species.

5. The method according to claim 4, wherein said alcohol in said alcohol-containing solvent is a saturated, unsaturated, or aromatic species, or a mixture thereof.

6. The method according to claim 4, wherein said non-alcoholic species includes at least one of the following: a carbonate/$CO_2$, dimethyl formamide (DMF), dimethyl sulfoxide (DMSO), acetonitrile, tetrahydrofuran (THF), acetone, N-methyl-2-pyrrolidone (NMP), chloroform, and ethyl acetate.

7. The method according to claim 4, wherein said alcohol serves as a nucleophile that mediates the formation said esters.

8. The method according to claim 4, wherein said alcohol is present in excess of stoichiometric amounts of said dialkylcarbonate.

9. The method according to claim 1, wherein at least 45% of said organic acid is converted into a yield of corresponding esters.

10. The method according to claim 9, wherein at least 70% of said carboxylic acid is converted to the ester.

11. The method according to claim 1, wherein said esters include either monoesters, diesters, or triesters, or a mixture containing combinations thereof.

12. The method according to claim 1, wherein said organic acid is converted into a corresponding monoester and diester in a ratio of about 95:0.5 to about 0.5:95.

13. The method according to claim 1, wherein a di-ester product is favored.

14. The method according to claim 1, wherein a $CO_2$ molecule is released from said reaction.

15. The method according to claim 1, wherein said esters are prepared in either a batch or a continuous process.

16. The method according to claim 1, wherein said method further comprises isolating said esters by at least fractional distillation, chromatography, or both from said reaction mixture.

17. The method according to claim 1, wherein said organic acid and dialkylcarbonate are reacted at a temperature between about 130° C. to about 230° C.

18. The method according to claim 17, wherein said temperature is between about 160° C. to about 215° C., at a pressure in a range from about 145 psi to about 950 psi in an inert atmosphere.

19. The method according to claim 1, wherein said organic acid and dialkylcarbonate are reacted within a time period not exceeding about 24 hours.

* * * * *